United States Patent
Wagner et al.

(10) Patent No.: US 7,361,138 B2
(45) Date of Patent: Apr. 22, 2008

(54) BIOABSORBABLE CASING FOR SURGICAL SLING ASSEMBLY

(75) Inventors: James Wagner, Sudbury, MA (US); Doreen Rao, Watertown, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 622 days.

(21) Appl. No.: 10/631,364

(22) Filed: Jul. 31, 2003

(65) Prior Publication Data
US 2005/0027220 A1  Feb. 3, 2005

(51) Int. Cl.
*A61F 2/02* (2006.01)
(52) U.S. Cl. .................................................. 600/30
(58) Field of Classification Search ............ 600/29–32, 600/37; 128/DIG. 25; 606/151, 154
See application file for complete search history.

(56) References Cited

U.S. PATENT DOCUMENTS

| | | |
|---|---|---|
| 246,648 A | 9/1881 | Wilcox |
| 1,030,530 A | 6/1912 | Palmer |
| 1,066,025 A | 7/1913 | Liberknecht |
| 1,179,910 A | 4/1916 | Greenfield |
| 1,310,982 A | 7/1919 | Davis |
| 1,417,669 A | 5/1922 | Langworthy |
| 1,517,787 A | 12/1924 | Langbein |
| 1,612,697 A | 12/1926 | Cecil |
| 1,677,671 A | 7/1928 | Councill |
| 2,113,246 A | 4/1938 | Wappler |
| 2,199,025 A | 4/1940 | Conn |
| 2,200,120 A | 5/1940 | Nauth |
| 2,454,680 A | 11/1948 | Stephens |
| 2,487,502 A | 11/1949 | Willinsky |
| 2,556,783 A | 6/1951 | Wallace |
| 2,635,238 A | 4/1953 | Garland |
| 2,655,921 A | 10/1953 | Haboush |
| 2,666,430 A | 1/1954 | Gispert |
| 2,671,444 A | 3/1954 | Pease, Jr. |
| 2,738,790 A | 3/1956 | Todt, Sr. et al. |
| 2,751,903 A | 6/1956 | Ivory et al. |
| 3,003,155 A | 10/1961 | Mielzynski et al. |
| 3,054,406 A | 9/1962 | Usher |
| 3,124,136 A | 3/1964 | Usher |

(Continued)

FOREIGN PATENT DOCUMENTS

CA      2198778     3/1996

(Continued)

OTHER PUBLICATIONS

Delome, E. La bandelette trans-obturatice: un procede mini-invasif pour traiter l'incontinence urinarire d'effort de la femme. Progres en Urologie. 11:1306-13 (2001) (English translation provided).

(Continued)

*Primary Examiner*—Samuel G Gilbert
(74) *Attorney, Agent, or Firm*—Ropes & Gray LLP

(57) ABSTRACT

The invention provides a surgical sling assembly for implanting in tissue to provide anatomical support in a patient. The surgical sling assembly includes a sling and a biocompatible casing enclosing at least a portion of the sling. The biocompatible casing is absorbed by the patient's tissues after the surgical sling assembly is positioned within the patient's tissue to provide anatomical support.

25 Claims, 4 Drawing Sheets

U.S. PATENT DOCUMENTS

| | | |
|---|---|---|
| 3,181,533 A | 5/1965 | Heath |
| 3,212,502 A | 10/1965 | Myers |
| 3,314,431 A | 4/1967 | Smith, Jr. |
| 3,364,200 A | 1/1968 | Ashton et al. |
| 3,388,847 A | 6/1968 | Kasulin et al. |
| 3,551,987 A | 1/1971 | Wilkinson |
| 3,565,073 A | 2/1971 | Giesy |
| 3,580,313 A | 5/1971 | McKnight |
| 3,593,903 A | 7/1971 | Astafiev et al. |
| 3,596,656 A | 8/1971 | Kaute |
| 3,620,212 A | 11/1971 | Fannon, Jr. et al. |
| 3,666,750 A | 5/1972 | Briskin et al. |
| 3,699,969 A | 10/1972 | Allen |
| 3,704,712 A | 12/1972 | Giesy et al. |
| 3,705,575 A | 12/1972 | Edwards |
| 3,710,592 A | 1/1973 | Scow |
| 3,739,784 A | 6/1973 | Itoh |
| 3,744,495 A | 7/1973 | Johnson |
| 3,823,705 A | 7/1974 | Trimble |
| 3,857,396 A | 12/1974 | Hardwick |
| 3,877,434 A | 4/1975 | Ferguson et al. |
| 3,890,977 A | 6/1975 | Wilson |
| 3,892,232 A | 7/1975 | Neufeld |
| 3,918,455 A | 11/1975 | Coplan |
| 3,995,619 A | 12/1976 | Glatzer |
| 4,006,747 A | 2/1977 | Kronenthal et al. |
| 4,085,756 A | 4/1978 | Weaver |
| 4,159,716 A | 7/1979 | Borchers |
| 4,172,458 A | 10/1979 | Pereyra |
| 4,175,557 A | 11/1979 | Hung |
| 4,193,137 A | 3/1980 | Heck |
| 4,217,890 A | 8/1980 | Owens |
| 4,347,847 A | 9/1982 | Usher |
| 4,371,124 A | 2/1983 | Gifford et al. |
| 4,391,869 A | 7/1983 | Cook et al. |
| 4,392,495 A | 7/1983 | Bayers |
| 4,400,833 A | 8/1983 | Kurland |
| 4,409,974 A | 10/1983 | Freedland |
| 4,414,967 A | 11/1983 | Shapiro |
| 4,415,111 A | 11/1983 | McHarrie et al. |
| 4,421,112 A | 12/1983 | Mains et al. |
| 4,422,567 A | 12/1983 | Haynes |
| 4,438,769 A | 3/1984 | Pratt et al. |
| 4,452,245 A | 6/1984 | Usher |
| 4,520,821 A | 6/1985 | Schmidt et al. |
| 4,527,726 A | 7/1985 | Assell et al. |
| 4,535,768 A | 8/1985 | Hourahane et al. |
| 4,537,185 A | 8/1985 | Stednitz |
| 4,545,374 A | 10/1985 | Jacobson |
| 4,549,545 A | 10/1985 | Levy |
| 4,569,469 A | 2/1986 | Mongeon et al. |
| 4,576,167 A | 3/1986 | Noiles |
| 4,606,335 A | 8/1986 | Wedeen |
| 4,606,343 A | 8/1986 | Conta et al. |
| 4,614,187 A | 9/1986 | Mulhollan et al. |
| 4,625,726 A | 12/1986 | Duthoy |
| 4,632,100 A | 12/1986 | Somers et al. |
| 4,633,871 A | 1/1987 | Shinozuka |
| 4,633,873 A | 1/1987 | Dumican et al. |
| 4,635,634 A | 1/1987 | Santos |
| 4,652,264 A | 3/1987 | Dumican |
| 4,655,219 A | 4/1987 | Petruzzi |
| 4,655,221 A | 4/1987 | Devereux |
| 4,664,305 A | 5/1987 | Blake, III et al. |
| 4,665,906 A | 5/1987 | Jervis |
| 4,669,473 A | 6/1987 | Richards et al. |
| 4,688,555 A | 8/1987 | Wardle |
| 4,691,705 A | 9/1987 | Okada |
| 4,705,040 A | 11/1987 | Mueller et al. |
| 4,738,255 A | 4/1988 | Goble et al. |
| 4,739,751 A | 4/1988 | Sapega et al. |
| 4,741,330 A | 5/1988 | Hayhurst |
| 4,741,335 A | 5/1988 | Okada |
| 4,744,353 A | 5/1988 | McFarland |
| 4,750,492 A | 6/1988 | Jacobs |
| 4,763,669 A | 8/1988 | Jaeger |
| 4,768,505 A | 9/1988 | Okada et al. |
| 4,769,038 A | 9/1988 | Bendavid et al. |
| 4,784,126 A | 11/1988 | Hourahane |
| 4,784,137 A | 11/1988 | Kulik et al. |
| 4,784,138 A | 11/1988 | Sinnett |
| 4,798,193 A | 1/1989 | Giesy et al. |
| 4,824,435 A | 4/1989 | Giesy et al. |
| 4,838,884 A | 6/1989 | Dumican et al. |
| 4,854,316 A | 8/1989 | Davis |
| 4,857,041 A | 8/1989 | Annis et al. |
| 4,870,957 A | 10/1989 | Goble et al. |
| 4,872,451 A | 10/1989 | Moore et al. |
| 4,873,977 A | 10/1989 | Avant et al. |
| 4,880,015 A | 11/1989 | Nierman |
| 4,883,048 A | 11/1989 | Purnell et al. |
| 4,889,119 A | 12/1989 | Jamiolkowski et al. |
| 4,898,156 A | 2/1990 | Gatturna et al. |
| 4,899,743 A | 2/1990 | Nicholson et al. |
| 4,905,692 A | 3/1990 | More |
| 4,909,789 A | 3/1990 | Taguchi et al. |
| 4,911,165 A | 3/1990 | Lennard et al. |
| 4,920,958 A | 5/1990 | Walt et al. |
| 4,920,986 A | 5/1990 | Biswas |
| 4,926,722 A | 5/1990 | Sorensen et al. |
| 4,938,760 A | 7/1990 | Burton et al. |
| 4,940,467 A | 7/1990 | Tronzo |
| 4,944,741 A | 7/1990 | Hasson |
| 4,945,920 A | 8/1990 | Clossick |
| 4,946,467 A | 8/1990 | Ohi et al. |
| 4,946,468 A | 8/1990 | Li |
| 4,957,498 A | 9/1990 | Caspari et al. |
| 4,960,420 A | 10/1990 | Goble et al. |
| 4,968,315 A | 11/1990 | Gatturna |
| 4,969,892 A | 11/1990 | Burton et al. |
| 4,973,300 A | 11/1990 | Wright |
| 4,978,351 A | 12/1990 | Rozas |
| 4,986,831 A | 1/1991 | King et al. |
| 4,997,433 A | 3/1991 | Goble et al. |
| 4,997,434 A | 3/1991 | Seedhom et al. |
| 4,997,436 A | 3/1991 | Oberlander |
| 5,002,550 A | 3/1991 | Li |
| 5,002,551 A | 3/1991 | Linsky et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,026,398 A | 6/1991 | May et al. |
| 5,030,219 A | 7/1991 | Matsen, III et al. |
| 5,036,867 A | 8/1991 | Biswas |
| 5,040,715 A | 8/1991 | Green et al. |
| 5,046,513 A | 9/1991 | Gatturna et al. |
| 5,052,607 A | 10/1991 | Dutton |
| 5,057,112 A | 10/1991 | Sherman et al. |
| 5,057,114 A | 10/1991 | Wittich et al. |
| 5,059,199 A | 10/1991 | Okada et al. |
| 5,061,181 A | 10/1991 | Niznick |
| 5,064,434 A | 11/1991 | Haber |
| 5,064,435 A | 11/1991 | Porter |
| 5,078,730 A | 1/1992 | Li |
| 5,078,731 A | 1/1992 | Hayhurst |
| 5,080,674 A | 1/1992 | Jacobs et al. |
| 5,084,058 A | 1/1992 | Li |
| 5,085,661 A | 2/1992 | Moss |
| 5,087,263 A | 2/1992 | Li |
| 5,088,323 A | 2/1992 | Johnson et al. |
| 5,089,013 A | 2/1992 | Bezwada et al. |
| 5,098,440 A | 3/1992 | Hillstead |

| Patent No. | Date | Inventor |
|---|---|---|
| 5,100,417 A | 3/1992 | Cerier et al. |
| 5,102,421 A | 4/1992 | Anspach, Jr. |
| 5,108,397 A | 4/1992 | White |
| 5,112,337 A | 5/1992 | Paulos et al. |
| 5,112,344 A | 5/1992 | Petros |
| 5,116,338 A | 5/1992 | Poggie et al. |
| 5,122,155 A | 6/1992 | Eberbach |
| 5,123,924 A | 6/1992 | Sioshansi et al. |
| 5,129,902 A | 7/1992 | Goble et al. |
| 5,133,723 A | 7/1992 | Li et al. |
| 5,141,520 A | 8/1992 | Goble et al. |
| 5,147,374 A | 9/1992 | Fernandez |
| 5,149,329 A | 9/1992 | Richardson |
| 5,152,279 A | 10/1992 | Wilk |
| 5,152,749 A | 10/1992 | Giesy et al. |
| 5,152,790 A | 10/1992 | Rosenberg et al. |
| 5,156,315 A | 10/1992 | Green et al. |
| 5,163,942 A | 11/1992 | Rydell |
| 5,163,946 A | 11/1992 | Li |
| 5,174,300 A | 12/1992 | Bales et al. |
| 5,176,692 A | 1/1993 | Wilk et al. |
| 5,178,630 A | 1/1993 | Schmitt |
| 5,180,388 A | 1/1993 | DiCarlo |
| 5,188,636 A | 2/1993 | Fedotov |
| 5,192,008 A | 3/1993 | Hwan |
| 5,192,303 A | 3/1993 | Gatturna et al. |
| 5,195,542 A | 3/1993 | Gazielly et al. |
| 5,197,968 A | 3/1993 | Clement |
| 5,203,784 A | 4/1993 | Ross et al. |
| 5,203,787 A | 4/1993 | Noblitt et al. |
| 5,207,679 A | 5/1993 | Li |
| 5,209,747 A | 5/1993 | Knoepfler |
| 5,217,462 A | 6/1993 | Asnis et al. |
| 5,217,486 A | 6/1993 | Rice et al. |
| 5,222,508 A | 6/1993 | Contarini |
| 5,224,946 A | 7/1993 | Hayhurst et al. |
| 5,236,445 A | 8/1993 | Hayhurst et al. |
| 5,242,457 A | 9/1993 | Akopov et al. |
| 5,250,033 A | 10/1993 | Evans et al. |
| 5,251,638 A | 10/1993 | Cottone, Jr. et al. |
| 5,254,130 A | 10/1993 | Poncet et al. |
| 5,254,133 A | 10/1993 | Seid |
| 5,256,133 A | 10/1993 | Spitz |
| 5,256,150 A | 10/1993 | Quiachon et al. |
| 5,258,000 A | 11/1993 | Gianturco |
| 5,258,016 A | 11/1993 | DiPoto et al. |
| 5,263,969 A | 11/1993 | Phillips |
| 5,268,001 A | 12/1993 | Nicholson et al. |
| 5,279,311 A | 1/1994 | Snyder |
| 5,281,237 A | 1/1994 | Gimpelson |
| 5,289,963 A | 3/1994 | McGarry et al. |
| 5,290,217 A | 3/1994 | Campos |
| 5,290,294 A | 3/1994 | Cox et al. |
| 5,292,328 A | 3/1994 | Hain et al. |
| 5,304,220 A | 4/1994 | Maginot |
| 5,311,858 A | 5/1994 | Adair |
| 5,312,433 A | 5/1994 | Boebel et al. |
| 5,328,077 A | 7/1994 | Lou |
| 5,333,624 A | 8/1994 | Tovey |
| 5,334,185 A | 8/1994 | Giesy et al. |
| 5,334,208 A | 8/1994 | Soehendra et al. |
| 5,337,736 A | 8/1994 | Reddy |
| 5,352,515 A * | 10/1994 | Jarrett et al. ............... 428/357 |
| 5,354,292 A | 10/1994 | Braeuer et al. |
| 5,356,064 A | 10/1994 | Green et al. |
| 5,362,294 A | 11/1994 | Seitzinger |
| 5,364,002 A | 11/1994 | Green et al. |
| 5,364,406 A | 11/1994 | Sewell, Jr. |
| 5,366,460 A | 11/1994 | Eberbach |
| 5,366,479 A | 11/1994 | McGarry et al. |
| 5,368,595 A | 11/1994 | Lewis |
| 5,368,602 A | 11/1994 | de la Torre |
| 5,370,282 A | 12/1994 | Sedlmeier |
| 5,370,650 A | 12/1994 | Tovey et al. |
| 5,370,662 A | 12/1994 | Stone et al. |
| 5,372,146 A | 12/1994 | Branch |
| 5,376,094 A | 12/1994 | Kline |
| 5,379,933 A | 1/1995 | Green et al. |
| 5,381,943 A | 1/1995 | Allen et al. |
| 5,383,477 A | 1/1995 | DeMatteis |
| 5,383,904 A | 1/1995 | Totakura et al. |
| 5,383,928 A | 1/1995 | Scott et al. |
| 5,395,349 A | 3/1995 | Quiachon et al. |
| 5,397,332 A | 3/1995 | Kammerer et al. |
| 5,411,506 A | 5/1995 | Goble et al. |
| 5,417,203 A | 5/1995 | Tovey et al. |
| 5,417,712 A | 5/1995 | Whittaker et al. |
| 5,423,860 A | 6/1995 | Lizardi et al. |
| 5,425,489 A | 6/1995 | Shichman et al. |
| 5,425,737 A | 6/1995 | Burbank et al. |
| 5,425,743 A | 6/1995 | Nicholas |
| 5,425,984 A | 6/1995 | Kennedy et al. |
| 5,431,173 A | 7/1995 | Chin et al. |
| 5,437,603 A | 8/1995 | Cerny et al. |
| 5,439,467 A | 8/1995 | Benderev et al. |
| 5,441,502 A | 8/1995 | Bartlett |
| 5,441,508 A | 8/1995 | Gazielly et al. |
| 5,443,482 A | 8/1995 | Stone et al. |
| 5,451,235 A | 9/1995 | Lock et al. |
| 5,456,722 A | 10/1995 | McLeod et al. |
| 5,474,543 A | 12/1995 | McKay |
| 5,499,991 A | 3/1996 | Garman et al. |
| 5,500,001 A | 3/1996 | Trott |
| 5,501,683 A | 3/1996 | Trott |
| 5,501,690 A | 3/1996 | Measamer et al. |
| 5,505,735 A | 4/1996 | Li |
| 5,507,754 A | 4/1996 | Green et al. |
| 5,507,796 A | 4/1996 | Hasson |
| 5,520,696 A | 5/1996 | Wenstrom, Jr. |
| 5,520,700 A | 5/1996 | Beyar et al. |
| 5,522,843 A | 6/1996 | Zang |
| 5,522,845 A | 6/1996 | Wenstrom, Jr. |
| 5,527,341 A | 6/1996 | Gogolewski et al. |
| 5,538,427 A | 7/1996 | Hoffman et al. |
| 5,540,703 A | 7/1996 | Barker, Jr. et al. |
| 5,544,664 A | 8/1996 | Benderev et al. |
| 5,549,617 A | 8/1996 | Green et al. |
| 5,549,619 A | 8/1996 | Peters et al. |
| 5,562,689 A | 10/1996 | Green et al. |
| 5,569,273 A | 10/1996 | Titone et al. |
| 5,571,117 A | 11/1996 | Ahn |
| 5,573,548 A | 11/1996 | Nazre et al. |
| 5,578,057 A | 11/1996 | Wenstrom, Jr. |
| 5,582,188 A | 12/1996 | Benderev et al. |
| 5,584,695 A | 12/1996 | Lal Sachdeva et al. |
| 5,584,835 A | 12/1996 | Greenfield |
| 5,591,163 A | 1/1997 | Thompson |
| 5,591,207 A | 1/1997 | Coleman |
| 5,601,575 A | 2/1997 | Measamer et al. |
| 5,607,432 A | 3/1997 | Fucci |
| 5,611,515 A | 3/1997 | Benderev et al. |
| 5,618,314 A | 4/1997 | Harwin et al. |
| 5,620,012 A | 4/1997 | Benderev et al. |
| 5,624,446 A | 4/1997 | Harryman, II |
| 5,634,931 A | 6/1997 | Kugel |
| 5,634,944 A | 6/1997 | Magram |
| 5,637,112 A | 6/1997 | Moore et al. |
| 5,641,502 A | 6/1997 | Skalla et al. |
| 5,641,566 A | 6/1997 | Kranzler et al. |
| 5,643,288 A | 7/1997 | Thompson |
| 5,643,320 A | 7/1997 | Lower et al. |
| 5,643,596 A | 7/1997 | Pruss et al. |
| 5,645,589 A | 7/1997 | Li |
| 5,645,849 A | 7/1997 | Pruss et al. |
| 5,645,915 A | 7/1997 | Kranzler et al. |
| 5,647,836 A | 7/1997 | Blake, III et al. |

| Patent | Date | Inventor |
|---|---|---|
| 5,649,940 A | 7/1997 | Hart et al. |
| 5,653,373 A | 8/1997 | Green et al. |
| 5,658,296 A | 8/1997 | Bates et al. |
| 5,660,854 A | 8/1997 | Haynes et al. |
| 5,662,654 A | 9/1997 | Thompson |
| 5,662,658 A | 9/1997 | Wenstrom, Jr. |
| 5,674,247 A | 10/1997 | Sohn |
| 5,681,301 A | 10/1997 | Yang et al. |
| 5,681,310 A | 10/1997 | Yuan et al. |
| 5,681,352 A | 10/1997 | Clancy, III et al. |
| 5,683,378 A | 11/1997 | Christy |
| 5,683,418 A | 11/1997 | Luscombe et al. |
| 5,690,649 A | 11/1997 | Li |
| 5,690,655 A | 11/1997 | Hart et al. |
| 5,690,677 A | 11/1997 | Schmieding et al. |
| 5,697,931 A | 12/1997 | Thompson |
| 5,700,266 A | 12/1997 | Harryman, II |
| 5,702,215 A | 12/1997 | Li |
| 5,702,397 A | 12/1997 | Goble et al. |
| 5,702,415 A | 12/1997 | Matthai et al. |
| 5,707,647 A | 1/1998 | Dunn et al. |
| 5,725,529 A | 3/1998 | Nicholson et al. |
| 5,725,557 A | 3/1998 | Gatturna et al. |
| 5,728,100 A | 3/1998 | Skiba |
| 5,733,337 A | 3/1998 | Carr, Jr. et al. |
| 5,742,943 A | 4/1998 | Chen |
| 5,749,884 A | 5/1998 | Benderev et al. |
| 5,752,963 A | 5/1998 | Allard et al. |
| 5,766,221 A | 6/1998 | Benderev et al. |
| 5,769,864 A | 6/1998 | Kugel |
| 5,782,834 A | 7/1998 | Lucey et al. |
| 5,782,862 A | 7/1998 | Bonutti |
| 5,785,640 A | 7/1998 | Kresch et al. |
| 5,788,710 A | 8/1998 | Bates et al. |
| 5,807,403 A | 9/1998 | Beyar et al. |
| 5,813,408 A | 9/1998 | Benderev et al. |
| 5,813,975 A | 9/1998 | Valenti |
| 5,814,051 A | 9/1998 | Wenstrom, Jr. |
| 5,814,071 A | 9/1998 | McDevitt et al. |
| 5,814,072 A | 9/1998 | Bonutti |
| 5,816,258 A | 10/1998 | Jervis |
| 5,824,082 A | 10/1998 | Brown |
| 5,827,291 A | 10/1998 | Fucci et al. |
| 5,836,314 A | 11/1998 | Benderev et al. |
| 5,836,315 A | 11/1998 | Benderev et al. |
| 5,836,961 A | 11/1998 | Kieturakis |
| 5,840,011 A | 11/1998 | Landgrebe et al. |
| 5,842,478 A | 12/1998 | Benderev et al. |
| 5,849,004 A | 12/1998 | Bramlet |
| 5,851,219 A | 12/1998 | Goble et al. |
| 5,860,993 A | 1/1999 | Thompson et al. |
| 5,868,747 A | 2/1999 | Ochoa et al. |
| 5,868,789 A | 2/1999 | Huebner |
| 5,871,503 A | 2/1999 | Bartlett |
| 5,899,906 A | 5/1999 | Schenk |
| 5,899,909 A | 5/1999 | Claren et al. |
| 5,916,225 A | 6/1999 | Kugel |
| 5,922,026 A | 7/1999 | Chin |
| 5,934,283 A | 8/1999 | Willem et al. |
| 5,935,122 A | 8/1999 | Fourkas et al. |
| 5,935,138 A | 8/1999 | McJames, II et al. |
| 5,935,172 A * | 8/1999 | Ochoa et al. ............ 623/23.36 |
| 5,954,057 A | 9/1999 | Li |
| 5,957,932 A | 9/1999 | Bates et al. |
| 5,972,000 A | 10/1999 | Beyar et al. |
| 5,989,180 A | 11/1999 | Norton |
| 5,997,541 A | 12/1999 | Schenk |
| 5,997,554 A | 12/1999 | Thompson |
| 6,001,104 A | 12/1999 | Benderev et al. |
| 6,010,447 A | 1/2000 | Kardjian |
| 6,030,337 A | 2/2000 | Grant et al. |
| 6,030,393 A | 2/2000 | Corlew |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,042,592 A | 3/2000 | Schmitt |
| 6,050,937 A | 4/2000 | Benderev |
| 6,053,935 A | 4/2000 | Brenneman et al. |
| 6,056,687 A | 5/2000 | Polyak et al. |
| 6,056,688 A | 5/2000 | Benderev et al. |
| 6,059,801 A | 5/2000 | Samimi |
| 6,068,591 A | 5/2000 | Bruckner et al. |
| 6,077,216 A | 6/2000 | Benderev et al. |
| 6,090,116 A | 7/2000 | D'Aversa et al. |
| 6,096,041 A | 8/2000 | Gellman et al. |
| 6,099,538 A | 8/2000 | Moses et al. |
| 6,099,547 A | 8/2000 | Gellman et al. |
| 6,102,921 A | 8/2000 | Zhu et al. |
| 6,110,101 A | 8/2000 | Tihon et al. |
| 6,113,611 A | 9/2000 | Allen et al. |
| 6,117,067 A | 9/2000 | Gil-Vernet |
| 6,168,801 B1 | 1/2001 | Heil, Jr. et al. |
| 6,200,261 B1 | 3/2001 | Deininger et al. |
| 6,200,330 B1 | 3/2001 | Benderev et al. |
| 6,221,005 B1 | 4/2001 | Bruckner et al. |
| 6,224,616 B1 | 5/2001 | Kugel |
| 6,231,581 B1 | 5/2001 | Shank et al. |
| 6,245,082 B1 | 6/2001 | Gellman et al. |
| 6,264,676 B1 | 7/2001 | Gellman et al. |
| 6,273,852 B1 | 8/2001 | Lehe et al. |
| 6,306,079 B1 | 10/2001 | Trabucco |
| 6,319,262 B1 | 11/2001 | Bates et al. |
| 6,319,272 B1 | 11/2001 | Brenneman et al. |
| 6,322,492 B1 | 11/2001 | Kovac |
| 6,328,686 B1 | 12/2001 | Kovac |
| 6,328,758 B1 | 12/2001 | Tornier et al. |
| 6,334,446 B1 | 1/2002 | Beyar |
| 6,355,065 B1 | 3/2002 | Gabbay |
| 6,382,214 B1 | 5/2002 | Raz et al. |
| 6,387,040 B1 | 5/2002 | Grant et al. |
| 6,387,041 B1 | 5/2002 | Harari et al. |
| 6,391,060 B1 | 5/2002 | Ory et al. |
| 6,406,234 B2 | 6/2002 | Frigg |
| 6,406,423 B1 | 6/2002 | Scetbon |
| 6,406,480 B1 | 6/2002 | Beyar et al. |
| 6,416,462 B1 | 7/2002 | Tovey et al. |
| 6,423,080 B1 | 7/2002 | Gellman et al. |
| 6,428,562 B2 | 8/2002 | Bonutti |
| 6,440,154 B2 | 8/2002 | Gellman et al. |
| 6,443,886 B2 | 9/2002 | Deininger et al. |
| 6,447,524 B1 | 9/2002 | Knodel et al. |
| 6,451,032 B1 | 9/2002 | Ory et al. |
| 6,461,291 B1 | 10/2002 | Polyak et al. |
| D466,213 S | 11/2002 | Snitkin et al. |
| 6,475,139 B1 | 11/2002 | Miller |
| 6,478,727 B2 | 11/2002 | Scetbon |
| 6,491,703 B1 | 12/2002 | Ulmsten |
| 6,494,887 B1 | 12/2002 | Kaladelfos |
| 6,500,194 B2 | 12/2002 | Benderev et al. |
| 6,502,578 B2 | 1/2003 | Raz et al. |
| 6,517,566 B1 | 2/2003 | Hovland et al. |
| 6,530,879 B1 | 3/2003 | Adamkiewicz |
| 6,530,943 B1 | 3/2003 | Hoepffner et al. |
| 6,582,443 B2 | 6/2003 | Cabak et al. |
| 6,596,001 B2 | 7/2003 | Stormby et al. |
| 6,596,002 B2 | 7/2003 | Therin et al. |
| 6,599,235 B2 | 7/2003 | Kovac |
| 6,605,097 B1 | 8/2003 | Lehe et al. |
| 6,612,977 B2 | 9/2003 | Staskin et al. |
| 6,638,209 B2 | 10/2003 | Landgrebe |
| 6,638,210 B2 | 10/2003 | Berger |
| 6,638,211 B2 | 10/2003 | Suslian et al. |
| 6,641,525 B2 | 11/2003 | Rocheleau et al. |
| 6,648,921 B2 | 11/2003 | Anderson et al. |
| 6,652,450 B2 | 11/2003 | Neisz et al. |

| | | | | | |
|---|---|---|---|---|---|
| 6,685,629 B2 | 2/2004 | Therin | DE | 32 06 846 A1 | 9/1983 |
| 6,755,781 B2 | 6/2004 | Gellman | DE | 33 40 581 C1 | 6/1985 |
| 6,802,807 B2 | 10/2004 | Anderson et al. | DE | 35 21 717 A1 | 12/1985 |
| 6,830,052 B2 | 12/2004 | Carter et al. | DE | 34 40 889 C1 | 6/1986 |
| 6,971,813 B2 * | 12/2005 | Shekalim et al. .......... 401/208 | DE | 86 04 065 U1 | 7/1986 |
| 2001/0000533 A1 | 4/2001 | Kovac | DE | 36 03 344 A1 | 8/1986 |
| 2001/0018549 A1 | 8/2001 | Scetbon | DE | 87 07 515 U1 | 9/1987 |
| 2001/0023356 A1 | 9/2001 | Raz et al. | DE | 37 09 706 A1 | 10/1987 |
| 2001/0049467 A1 | 12/2001 | Lehe et al. | DE | 87 07 516 U1 | 10/1987 |
| 2002/0013590 A1 | 1/2002 | Therin et al. | DE | 37 14 560 A1 | 11/1987 |
| 2002/0022841 A1 | 2/2002 | Kovac | DE | 37 04 094 A1 | 8/1988 |
| 2002/0028980 A1 | 3/2002 | Thierfelder et al. | DE | 37 09 067 A1 | 9/1988 |
| 2002/0052654 A1 | 5/2002 | Darois et al. | DE | 37 39 254 A1 | 6/1989 |
| 2002/0055748 A1 | 5/2002 | Gellman et al. | DE | 40 24 636 A1 | 2/1992 |
| 2002/0068948 A1 | 6/2002 | Stormby et al. | DE | 41 31 176 A1 | 4/1993 |
| 2002/0072694 A1 | 6/2002 | Snitkin et al. | DE | 42 12 430 A1 | 10/1993 |
| 2002/0077526 A1 | 6/2002 | Kammerer et al. | EP | 0 140 557 A3 | 5/1985 |
| 2002/0082619 A1 | 6/2002 | Cabak et al. | EP | 0 153 831 A3 | 9/1985 |
| 2002/0091298 A1 | 7/2002 | Landgrebe | EP | 0 160 870 | 11/1985 |
| 2002/0091373 A1 | 7/2002 | Berger | EP | 0 241 240 A2 | 10/1987 |
| 2002/0099258 A1 | 7/2002 | Staskin et al. | EP | 0 281 763 A2 | 9/1988 |
| 2002/0099259 A1 | 7/2002 | Anderson et al. | EP | 0 334 046 B1 | 9/1989 |
| 2002/0099260 A1 | 7/2002 | Suslian et al. | EP | 0 337 918 B1 | 10/1989 |
| 2002/0107430 A1 | 8/2002 | Neisz et al. | EP | 0 417 031 A2 | 3/1991 |
| 2002/0116025 A1 | 8/2002 | Haab | EP | 0 437 063 A2 | 7/1991 |
| 2002/0127270 A1 | 9/2002 | Li et al. | EP | 0 437 063 A3 | 7/1991 |
| 2002/0128670 A1 | 9/2002 | Ulmsten et al. | EP | 0 450 608 A1 | 10/1991 |
| 2002/0138025 A1 | 9/2002 | Gellman et al. | EP | 0 484 671 A2 | 5/1992 |
| 2002/0143234 A1 | 10/2002 | LoVuolo | EP | 0 538 984 B1 | 4/1993 |
| 2002/0147382 A1 | 10/2002 | Neisz et al. | EP | 0 555 103 A1 | 8/1993 |
| 2002/0151762 A1 | 10/2002 | Rocheleau et al. | EP | 0 558 993 A2 | 9/1993 |
| 2002/0151909 A1 | 10/2002 | Gellman et al. | EP | 0 565 049 A1 | 10/1993 |
| 2002/0151910 A1 | 10/2002 | Gellman et al. | EP | 0 571 057 A1 | 11/1993 |
| 2002/0156487 A1 | 10/2002 | Gellman et al. | EP | 0 598 607 A2 | 5/1994 |
| 2002/0156488 A1 | 10/2002 | Gellman et al. | EP | 0 599 772 A1 | 6/1994 |
| 2002/0156489 A1 | 10/2002 | Gellman et al. | EP | 0 677 297 | 10/1995 |
| 2002/0161382 A1 | 10/2002 | Neisz et al. | EP | 0 686 373 A1 | 12/1995 |
| 2002/0165566 A1 | 11/2002 | Ulmsten | EP | 0 854 691 B1 | 7/1998 |
| 2002/0188169 A1 | 12/2002 | Kammerer et al. | EP | 0 778 749 B1 | 12/2000 |
| 2003/0004395 A1 | 1/2003 | Therin | EP | 1 151 722 A2 | 7/2001 |
| 2003/0004580 A1 | 1/2003 | Sump et al. | EP | 1 159 921 A2 | 12/2001 |
| 2003/0009181 A1 | 1/2003 | Gellman et al. | EP | 1 151 722 A3 | 1/2002 |
| 2003/0010929 A1 | 1/2003 | Priewe et al. | FR | 2 432 861 | 3/1980 |
| 2003/0023135 A1 | 1/2003 | Ulmsten et al. | FR | 2 718 012 | 10/1995 |
| 2003/0023136 A1 | 1/2003 | Raz et al. | FR | 2 739 016 | 3/1997 |
| 2003/0023137 A1 | 1/2003 | Gellman | GB | 2 151 142 A | 7/1985 |
| 2003/0023138 A1 | 1/2003 | Luscombe | GB | 2 214 814 A | 9/1989 |
| 2003/0028075 A1 | 2/2003 | Ulmsten et al. | GB | 2 268 690 A | 1/1994 |
| 2003/0036676 A1 | 2/2003 | Scetbon | GB | 2 353 220 | 2/2001 |
| 2003/0045774 A1 | 3/2003 | Staskin et al. | GB | 2 359 256 | 8/2001 |
| 2003/0045892 A1 | 3/2003 | Kaladelfos | JP | 63 095945 | 4/1988 |
| 2003/0050530 A1 | 3/2003 | Neisz et al. | JP | 6-114067 | 4/1994 |
| 2003/0062052 A1 | 4/2003 | Carter et al. | SE | 503 271 | 3/1996 |
| 2003/0065246 A1 | 4/2003 | Inman et al. | SE | 506 164 | 4/1997 |
| 2003/0100954 A1 | 5/2003 | Schuldt-Hempe et al. | SU | 990 220 A | 1/1983 |
| 2003/0114866 A1 | 6/2003 | Ulmsten et al. | SU | 1225547 | 4/1986 |
| 2003/0130670 A1 | 7/2003 | Anderson et al. | SU | 1443873 | 12/1988 |
| 2003/0171644 A1 | 9/2003 | Anderson et al. | WO | 88/01853 | 3/1988 |
| 2003/0176762 A1 | 9/2003 | Kammerer | WO | 89/04674 A | 6/1989 |
| 2003/0176875 A1 | 9/2003 | Anderson et al. | WO | 89/10096 | 11/1989 |
| 2003/0191480 A1 | 10/2003 | Ulmsten et al. | WO | 91/02493 | 3/1991 |
| 2003/0212305 A1 | 11/2003 | Anderson et al. | WO | 92/05828 | 4/1992 |
| 2004/0225181 A1 * | 11/2004 | Chu et al. ..................... 600/37 | WO | 92/16152 | 10/1992 |
| 2004/0243166 A1 | 12/2004 | Odermatt et al. | WO | 92/21298 | 12/1992 |
| 2004/0249240 A1 | 12/2004 | Goldmann et al. | WO | 93/10715 | 6/1993 |
| 2005/0010078 A1 | 1/2005 | Jamiolkowski | WO | 93/10731 | 6/1993 |
| 2005/0010306 A1 | 1/2005 | Priewe et al. | WO | 93/19678 | 10/1993 |
| 2005/0027368 A1 | 2/2005 | Hellhammer et al. | WO | 94/04080 | 3/1994 |
| | | | WO | 94/05223 | 3/1994 |
| | FOREIGN PATENT DOCUMENTS | | WO | 94/19029 | 9/1994 |
| | | | WO | 94/28799 | 12/1994 |
| DE | 24 28 319 | 1/1976 | WO | 95/05129 | 2/1995 |
| DE | 25 32 242 | 2/1977 | WO | 96/06567 | 3/1996 |

| | | |
|---|---|---|
| WO | 96/25887 | 8/1996 |
| WO | 96/28100 | 9/1996 |
| WO | 97/06731 | 2/1997 |
| WO | 97/13465 | 4/1997 |
| WO | WO-97/13465 | 4/1997 |
| WO | 97/30638 | 8/1997 |
| WO | 97/41792 | 11/1997 |
| WO | 97/43982 | 11/1997 |
| WO | 98/12971 | 4/1998 |
| WO | 98/35632 | 8/1998 |
| WO | WO-98/34545 | 8/1998 |
| WO | 00/66030 | 11/2000 |
| WO | 00/74594 | 12/2000 |
| WO | 00/74613 | 12/2000 |
| WO | 00/74633 | 12/2000 |
| WO | 01/52750 | 7/2001 |
| WO | WO-02/19945 | 3/2002 |
| WO | WO-02/32321 | 4/2002 |
| WO | WO-03/007847 | 1/2003 |
| WO | WO-2005/007019 | 1/2005 |

OTHER PUBLICATIONS

Giesy et al. Ureteral instrumentation: A New System for Continued Access Via a Safety Guidewire. Journal of Urology. No. 4, Part 2, p. 282A (1988).

Haab et al. Feasibility of Outpatient Percutaneous Bladder Neck Suspension Under Local Anesthesia. Urology. 50:4, 585-897 (1997).

Jacquetin, B. Utilisation du TVT dans la chirurgie de l'incontinence urinaire feminine. J. Gynecol Obstet Biol Reprod. 29, 242-47 (2000).

Norris et al. Use of Synthetic Material in Sling Surgery: A Minimally Invasive Approach. Journal of Endourology. 10:3, 227-30 (1996).

Petros, P. An Integral Theory of Bladder Neck Opening, Closure and Urinary Incontinence in the Female. International Journal of Gynecology & Obstetrics. XXIII World Congress of Gynaecology and Obstetrics (FIGO) 1991.

Petros, P. Medium-term Follow-up of the Intravaginal Slingplasty Operation Indicates Minimal Deterioration of Urinary Continence with Time. Aust NZ J Obstet Gynaecol. 39:3, 354-56 (1999).

Raz et al. Vaginal Wall Sling. The Journal of Urology. 141:43-6 (1989).

Raz et al. Fascial Sling to Correct Mail Neurogenic Sphincter Incompetence: The McGuire/Raz Approach. Journal of Urology. vol. 139: 528-531 (1988).

Schostak et al., "Transvaginal bone anchors in femal stress urinary incontinence: Poor Results." Gynecologic and Obstetric Investigation, vol. 54, No. 3, pp. 154-158, 2002.

Staskin et al. The Gore-tex sling procedure for female sphincteric incontinence:indications, technique, and results. World J of Urol. 15:5, 295-99 (1997).

Staskin, D.R. Sling Surgery for the Treatment of Female Stress Incontinence. 5:1, 106-22 (1991).

Sussman, et al. The Raz Bladder Neck Suspension: Five-Year Experience. The Journal of Urology. 145, 223A (1993).

Ulmsten et al. A Multicenter Study of Tension-Free Vaginal Tape (TVT) for Surgical Treatment of Stress Urinary Incontinence. Int Urogynecol J. 9:4, 210-13 (1998).

Ulmsten et al. Surgery for female urinary incontinence. Current Opinion in Obstetrics & Gynecology. 4:3, 456-62 (1992).

Ulmsten et al. Connective Tissue Factors in the Aetiology of Female Pelvic Disorders. Ann. Med. 22:6, 3 (1990).

Ulmsten, U. An Introduction to Tension-Free Vaginal Tape (TVT)—A New Surgical Procedure for Treatment of Female Urinary Incontinence. Int Urogynecol J. (Suppl 2): S3-4 (2001).

Ulmsten, U. The basic understanding and clinical results of tension-free vaginal tape for stress urinary incontinence. Der Urologe [A] 40:269-73 (2001).

A Superior Approach to Tensionless Sling Placement, SPARC sling system for stress urinary incontinence, American Medical Systems, Inc., 4 pages (2001).

Adamiak et al., "The Efficacy and Safety of the Tension-Free Vaginal Tape Procedure Do Not Depend on the Method of Analgesia", European Urology, 2002, vol. 42, pp. 29-33.

Agarwala et al., "Minimally invasive management of urinary incontinence", Current Opinion in Obstetrics and Gynecology, 2002, vol. 14, No. 4, pp. 429-433.

Araki et al., "The Loop-Loosening Procedure for Urination Difficulties after Stamey Suspension of the Vesical Neck," The Journal of Urology, Aug. 1990, vol. 144, pp. 319-323.

Bayer et al., "A New Approach to Primary Strengthing of Colostomy with Marlex® Mesh to Prevent Paracolostomy Hernia," Surgery, Gynecology & Obstetrics, Dec. 1986, vol. 163, pp. 579-580.

Beck et al., "A 25-Year Experience with 519 Anterior Colporrhaphy Procedures," Obstetrics & Gynecology, Dec. 1991, vol. 78, No. 6, pp. 1011-1018.

Benderev, "A New Endoscopic Bladder Neck Suspension for the Outpatient Treatment of Stress urinary Incontinence," The Journal of Urology, Apr. 1993, No. 4, videotape, V-40, p. 197A.

Benderev, "A Modified Percutaneous Outpatient Bladder Neck Suspension System," The Journal of Urology, Dec. 1994, vol. 152, pp. 2316-2320.

Benderev, "Anchor Fixation and Other Modifications of Endoscopic Bladder Neck Suspension," Urology, Nov. 1992, vol, 40, No. 5, pp. 409-418.

Blaivas, "Pubovaginal Fascial Sling for the Treatment of Complicated Stress Urinary Incontinence," The Journal of Urology , Jun. 1991, vol. 145, pp. 1214-1218.

Blaivas, "Successful Pubovaginal Sling Surgery," Contemporary Urology, Jul. 1993, pp. 40-63.

Brenner, "Mesh Materials in Hernia Repair," Expert Meeting on Hernia Surgery, St. Moritz, 1994. Basel Karger, 1995, pp. 172-179.

Cruikshank, "Reconstructive Procedures for the Gynecologic Surgeon," American Journal of Obstetrics and Gynecology, Feb. 1993, vol. 168, No. 2, pp. 469-475.

DeLancey, "Structural Support of the Urethra as it Relates to Stress urinary Incontinence: The Hammock Hypothesis," American Journal of Obstetrics and Gynecology, Jun. 1994, vol. 170, No. 6, pp. 1713-1723.

Falconer et al., "Clinical Outcome and Changes in Connective Tissue Metabolism after Intravaginal Slingplasty in Stress Incontinent Women," The International Urogynecology Journal, 1996, vol. 7, 133-137.

Falk et al., United States Statutory Invention Registration, Reg. No. H1028, Mar. 3, 1992, United States Patent Office, Washington D.C.

Fianu et al., "Absorbable Polyglactin Mesh for Retropubic Sling Operations in Female Urinary Stress Incontinence", Scandinavian Journal of Urology and Nephrology, Mar. 1985, vol. 29, No. 1, pp. 45-50.

Forneret et al., "Cost-Effective Treatment of Female Stress Urinary Incontinence: Modified Pereyra Bladder Neck Suspension," Urology, Apr. 1985, vol. 25, No. 4, pp. 365-367.

Gittes et al., "No-Incision Pubovaginal Suspension for Stress Incontinence," The Journal of Urology, Sep. 1987, vol. 138, pp. 568-570.

Hancock et al., "Transpubic Suspension of the Bladder Neck for Urinary Incontinence," The Journal of Urology, May 1980, vol. 123, pp. 667-668.

Henriksen et al., "A Urodynamic Comparison between Abdominal Urethrocystopexy and Vaginal Sling Plasty in Female Stress Incontinence", Urologia Internationalis, 1978, vol. 33, No. 1-3, pp. 111-116.

Henriksson, et al., "A urodynamic evaluation of the effects of abdominal urethrocystpexy and vaginal sling urethroplasty in women with stress incontinence", American Journal of Obstetrics and Gynecology, 1978, vol. 131, No. 1, pp. 77-82.

Hoffman et al., "Transvestibular Retropubic Bladder Neck Suspension: A Pilot Study," The Journal of Reproductive Medicine, Mar. 1995, vol. 40, No. 3, pp. 181-184.

Inglesia et al., "The Use of Mesh in Gynecologic Surgery," International Urogynecology Journal, 1997, vol. 8, pp. 105-115.

Iosif et al., "Urodynamic studies of women with prolapse and stress incontinence before and after surgical repair", Zentralblatt für Gynäkologie, 1979, vol. 101, pp. 1433-1442.

Kersey, "The gauze hammock sling operation in the treatment of stress incontinence", British Journal of Obstetrics and Gynaecology, Oct. 1983, vol. 90, pp. 945-949.

Kovac et al., "Pubic Bone Suburethral Stabilization Sling for Recurrent Urinary Incontinence," Obstetrics & Gynecology, Apr. 1997, vol. 89, No. 4, pp. 624-627.

Leach et al., "Modified Pereyra Bladder Neck Suspension after Previously Failed Anti-Incontinence Surgery," Urology, Apr. 1984, vol. 23, No. 4, pp. 359-362.

Leach et al., "Percutaneous Bladder Neck Suspension," Urologic Clincs ofNorth America, Aug. 1996, vol. 23, No. 3, pp. 511-516.

Leach, "Bone Fixation Technique for Transvaginal Needle Suspension", Urology, May 1988, vol. 31, No. 5, pages 388-390.

Mascio, et al., "Therapy of Urinary Stress Incontinence in Women Using Mitek® GII Anchors," The Mitek Brochure, 1993.

Mattox et al., "Modification of the Miya Hook in Vaginal Colpopexy," The Journal of Reproductive Medicine, Oct. 1995, vol. 40, No. 10, pp. 681-683.

McKiel et al., Marshall-Marchetti Procedure: Modification, The Journal of Urology, 1966, vol. 96, pp. 737-739.

Mitchell, et al., "Hook Needle and Retractor for Posterior Urethroplasty," British Journal of Urology, 1970, vol. 42, pp. 599-600.

Nativ et al., "Bladder Neck Suspension Using Bone Anchors for the Treatment of Female Stress Incontinence," ASAIO Journal, 1997, pp. 204-208.

Nichols et al., "Identification of Pubourethal Ligaments and their Role in Transvaginal Surgical Correction of Stress Incontinence," American Journal of Obstetrics and Gynecology, Jan. 1973, vol. 115, No. 1, pp. 123-128.

Pereyra, "A Simplified Surgical Procedure for the Corection of Stress Incontinence in Women," West. J. Surg. Obstetrics and Gynecology, Jul.-Aug. 1959, pp. 223-226.

Petros et al., "An Integral Theory and its Method for the Diagnosis and Management of Female Urinary Incontinence", Scandinavian Journal of Urology and Nephrology, 1993, Supplement No. 153.

Petros et al., "The Autogenic Ligament Procedure: A Technique for Planned Formation of an Artificial Neo-Ligament", Acta Obstetricia et Gynecologica Scandinavica, 1990, vol. 69, Supplement 153, pp. 43-51.

Petros et al., "The Tuck Procedure: A Simplified Vaginal Repair for Treatment of Female Urinary Incontinence", Acta Obstetricia et Gynecologica Scandinavica, 1990, vol. 69, Supp. 153, pp. 41-42.

Petros et al., "Urethral Pressure Increase on Effort Originates from within the Urethra, and Continence from Musculovaginal Closure", Neurourology and Urodynamics, 1995, vol. 14, No. 4, pp. 337-350.

Petros, "Ambulatory Surgery for Urinary Incontinence and Vaginal Prolapse," The Medical Journal of Australia, Jul. 1994, vol. 161, pp. 171-172.

Petros, "The Intravaginal Slingplasty Operation, a Minimally Invasive Technique for Cure of Urinary Incontinence in the Female", Aust. NZ Journal of Obstetrics & Gynaecology, 1996, 36:4, pp. 453-461.

Raz, "Modified Bladder Neck Suspension for Female Stress incontinence," Urology, Jan. 1981, vol. 17, No. 1, pp. 82-85.

Rezapour et al., "Tension-Free Vaginal Tape (TVT) in Woman with Recurrent Stress Urinary Incontinence—A Long-term Follow up", International Urogynecology Journal, 2001, vol. 12 (Suppl 2), pp. S9-S11.

Riachi et al., "Repeat Tension-Free Transvaginal Tape (TVT) Sling for the Treatment of Recurrent Stress Urinary Incontinence", International Urogynecology Journal, 2002, vol. 13, No. 2, pp. 133-135.

Richardson et al., "Treatment of Stress Urinary Incontinence Due to Paravaginal Fascial Defect," Obstetrics & Gynecology, Mar. 1981, vol. 57, No. 3, pp. 357-362.

Richmond et al., "Modification of the Bankart Reconstruction with a Suture Anchor," The American Journal of Sports Medicine, 1991, vol. 19, No. 4, pp. 343-346.

Robertson et al., "Soft Tissue Fixation to Bone," The Journal of Sports Medicine, 1986, vol. 14, No. 5, pp. 398-403.

Schaeffer et al., "Endoscopic Suspension of Vesical Neck for Urinary Incontinence," Urology, May 1984, vol. 23, No. 5, pp. 484-494.

Schatzker et al., "The Rationale of Operative Fracture Care," 1987, pp. XIV-XV and 159.

Scheuter, "The Modified Pereyra Bladder Neck Suspension Procedure Using Mitek® GII Anchors," The Mitek Brochure, 1993.

Spencer et al., "A Comparison of Endoscopic Suspension of the Vesical Neck with Suprapubic Vesicourethropexy for Treatment of Stress Urinary Incontinence," The journal of Urology, Mar. 1987, vol. 137, pp. 411-415.

Stamey, "Endoscopic Suspension of the Vesical Neck for Urinary Incontinence in Females," Ann. Surg., Oct. 1980, vol. 192, No. 4, pp. 465-471.

Stamey, "Endoscopic Suspension of the Vesical Neck for Urinary Incontinence," Surgery, Gynecology & Obstetrics, Apr. 1973, vol. 136, No. 4, pp. 547-554.

Stamey, "Endoscopic Suspension of the Vesical Neck," 1986, pp. 115-132.

Tension-Free Support for Incontinence, 1, 2, 3, 4, 5 Years of Proven Performance, Lasting freedom for your SUI patients, Gynecare TVT, 6 pages (2002).

The essence of a contemporary synthetic sling self-anchoring complete adjustability elastic, Safyre™ Autofixation System, Promedon, 4 pages (2002).

Trockman et al., " Modified Pereyra Bladder Neck Suspension: 10-Year Mean Follow Up Using Outcomes Analysis in 125 Patents," The Journal of Urology, Nov. 1995, vol. 154, pp. 1841-1847.

Ulmsten et al., "A three-year follow up of tension free vaginal tape for surgical treatment of female stress urinary incontinence", British Journal of Obstetrics and Gynecology, Apr. 1999, vol. 106, pp. 345-350.

Ulmsten et al., "An Ambulatory Surgical Procedure Under Local Anesthesia for Treatment of Female Urinary Incontinence," International Urogynecology Journal, 1996, vol. 7, pp. 81-86.

Ulmsten et al., "Intravaginal Slingplasty (IVS): An Ambulatory Surgical Procedure for Treatment of Female Urinary Incontinence," Scandinavian Journal of Urology and Nephrology, Mar. 1995, vol. 29, No. 1, pp. 75-82.

Ulmsten et al., "Intravaginal Slingplasty", Zentralbl Gynakol, 116 (1994), pp. 398-404.

Urken, "About Lifecell—Our Science," Lifecell, 2001.

Vasavada et al., "Incisionless Pubovaginal Fascial Sling Using Transvaginal Bone Anchors for the Treatment of Stress Urinary Incontinence," Digital Urology Journal, 2001.

Wang et al., "Tension-Free Vaginal Tape, A Minimally Invasive Solution to Stress Urinary Incontinence in Women", The Journal of Reproductive Medicine, May 1998, vol. 43, No. 5, pp. 429-434.

Webster et al., "Voiding Dysfunction Follow-up Cystourethropexy: Its Evaluation and Management," The Journal of Urology, Sep. 1990, vol. 144, pp. 670-673.

Webster, "Female Urinary Incontinence," Urologic Surgery, 1983, Third Edition, pp. 665-679.

Winter, "Peripubic Urethropexy for Urinary Stress Incontinence in Women," Urology Oct. 1982, vol. 20, No. 4, pp. 408-411.

Zacharin, "Abdonimoperineal Urethral Suspension in the Management of Recurrent Stress Incontinence of Urine—A 15-Year Experience," Obstetrics & Gynecology, Nov. 1983, vol. 62, No. 5, pp. 644-654.

Zimmern et al., "A Prospective Evaluation of Four-Corner Bladder Neck Suspension for Grade II/III Cystocele Repair," Neurology and Urodynamics, 1990, vol. 9, pp. 195 and 231.

Zimmern et al., "Transvaginal Closure of the Bladder Neck, " Seminars in Urology, Feb. 1986, vol. 4, No. 1, pp. 30-32.

* cited by examiner

BIOABSORBABLE CASING FOR SURGICAL SLING ASSEMBLY

TECHNICAL FIELD

The invention generally relates to surgical sling assemblies, and related methods, for providing anatomical support in a patient's body. More particularly, the invention relates to surgical sling assemblies, and related methods, that include bioabsorbable casings.

BACKGROUND INFORMATION

Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results.

A popular treatment of SUI is the use of a surgical sling that is placed under a patient's bladder neck or mid-urethra to provide a urethral platform. Placement of the surgical sling limits the endopelvic fascia drop while providing compression to the urethral sphincter to improve coaptation. Typically, a protective sleeve encloses the sling during the placement procedure. Once the surgical sling assembly, which includes the sling and the sleeve, is correctly positioned in the patient's periurethral tissues, the sleeve is physically removed from about the sling and withdrawn from the patient's body, leaving behind only the sling in the patient's tissues.

The current steps and procedures used to physically remove the sleeve from about the sling which it encloses are, however, problematic. For instance, while physically removing the sleeve from about the sling, friction between the sleeve and the sling may cause the sling to be dragged away from its preferred position adjacent the mid-urethra, to twist, or to otherwise become misplaced. Ultimately, the utility of the sling is hampered and patient discomfort is increased.

Improved surgical sling assemblies, and related methods, for treating SUI are, therefore, needed.

SUMMARY OF THE INVENTION

The present invention provides a surgical sling assembly, and related methods, for providing anatomical support in a patient's body (e.g., a surgical sling assembly for treating urinary incontinence in a patient). The surgical sling assembly, and related methods, of the invention have the advantage of obviating the need to physically remove a sleeve from about a sling.

In one aspect of the invention, a surgical sling assembly for implanting in tissue to provide anatomical support in a patient includes a sling and a biocompatible casing. The biocompatible casing encloses at least a portion of the sling and includes a bioabsorbable material. The biocompatible casing is absorbed by the patient's tissues after the surgical sling assembly is positioned within the patient's tissue to provide anatomical support. As the term is used herein, bioabsorbable means removal of a substance in a patient's tissue by physiologic or pathologic means.

In one embodiment of this aspect of the invention, the biocompatible casing includes a sleeve. Alternatively, the biocompatible casing includes a coating. The bioabsorbable material may be an alginate, a sugar based formulation, a starch, a gelatin, cellulose, polyvinyl alcohol, polyglycolic acid, polylactic acid, polydioxinone, or a lubricious material. In one embodiment, the surgical sling assembly is positioned within a patient's periurethral tissues to treat urinary incontinence. In one such embodiment, the biocompatible casing is absorbed by the patient's tissues in less than ten minutes after the surgical sling assembly is positioned within the patient's periurethral tissues. In one such particular embodiment, the biocompatible casing is absorbed by the patient's tissues in eight to ten minutes after the surgical sling assembly is positioned within the patient's periurethral tissues.

In another aspect, the invention relates to a method for providing anatomical support in a patient. The method includes providing a surgical sling assembly as described above and positioning the sling within the patient's tissues.

In one embodiment of this aspect of the invention, the sling is positioned within a patient's periurethral tissues to treat urinary incontinence.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DESCRIPTION

In general, the invention pertains to surgical sling assemblies, and related methods, for providing anatomical support in a patient's body (e.g., a surgical sling assembly for the treatment of urinary incontinence). All of the embodiments have in common a sling at least partially enclosed within a bioabsorbable casing.

Figure 1:
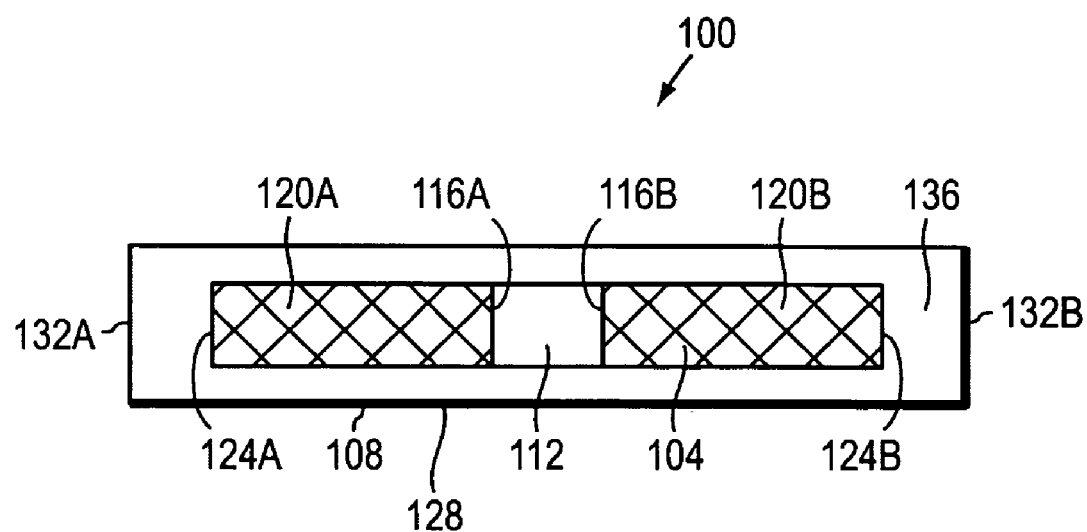
FIG. 1 depicts a top view of a sling assembly according to an illustrative embodiment of the invention.

FIG. 1 depicts a surgical sling assembly 100 according to an illustrative embodiment of the invention. In the illustrative embodiment, the surgical sling assembly 100 includes a sling 104 and a casing 108. The sling 104 is, for example, generally rectangular in shape and flat, or sheet-like. In a preferred embodiment, the sling 104 is a mesh sling. In one embodiment, the sling 104 is knit from fibers, such as, for example, polymeric fibers. However, in alternative embodiments, the sling 104 may be made of any suitable materials, including, for example, native mammalian tissue or any combination of the above materials. In the illustrative embodiment, the sling 104 includes a mid-length portion 112, which has end points 116A, 116B, and two end-length portions 120A, 120B. The two end-length portions 120A, 120B extend from the end points 116A, 116B of the mid-length portion 112 to sling ends 124A, 124B, respectively. The two end-length portions 120A, 120B are, in one embodiment, of substantially equal length, such that the mid-length portion 112 is generally centered along the long axis of the sling 104. Alternatively, in another embodiment, the two end-length portions 120A, 120B are of different lengths and the mid-length portion 112 is eccentric (not shown).

Figure 2:
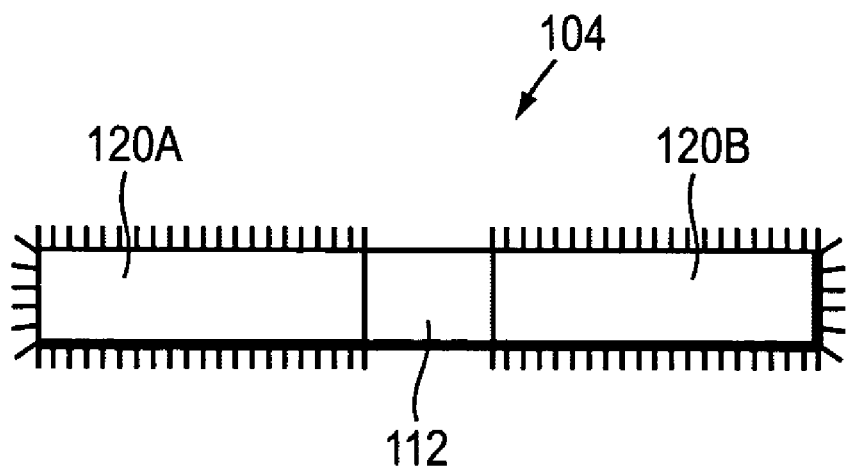
FIG. 2 depicts a top view of a sling according to an illustrative embodiment of the invention.

FIG. 2 depicts a sling 104 according to an illustrative embodiment of the invention. In the illustrative embodiment, the end-length portions 120A, 120B are tanged (i.e., rough) portions of the sling 104 that, as described below, engage the patient's periurethral tissues and secure the sling 104 in position. For example, in one embodiment, fiber ends extend/project from the tanged end-length portions 120A, 120B. For its part, the mid-length portion 112 is, in the illustrative embodiment, a de-tanged (i.e., a smooth) portion of the sling 104 that is preferably placed under the patient's mid-urethra. For example, in one embodiment, the de-tanged mid-length portion 112 is heat sealed to remove any sharp fiber ends and to ensure that its surfaces remain smooth.

The casing 108 encloses at least a portion of the sling 104. In one embodiment, as illustrated in FIG. 1, the casing 108 encloses the entire sling 104. In another embodiment, the casing 108 encloses only the tanged end-length portions 120A, 120B of the sling 104. In yet another embodiment, the casing 108 encloses the tanged end-length portions 120A, 120B and a portion of one or both sides of the de-tanged mid-length portion 112.

According to the illustrative embodiment shown in FIG. 1, the casing 108 is a sleeve 128, e.g., a flattened tube. The sleeve 128 may include one or more layers of the same or different materials that are laminated together. In one embodiment, the sleeve 128 includes a first sleeve-end 132A, a second sleeve-end 132B, and a lumen 136 extending from the first sleeve-end 132A to the second sleeve-end 132B. Throughout the process of delivering the sling 104 to the patient's periurethral tissues, the sling 104 is located within the lumen 136 of the sleeve 128, between the first sleeve-end 132A and the second sleeve-end 132B, as illustrated. As such, the tanged end-length portions 120A, 120B of the sling 104 are protected by the sleeve 128, thereby preventing the tanged end-length portions 120A, 120B from catching on the patient's tissues during the delivery procedure. The casing 108 maintains the sling 104 in a flat configuration and prevents it from twisting, turning, or otherwise becoming distorted, or even destroyed, during implantation of the sling 104 in the patient's body.

Figure 3:
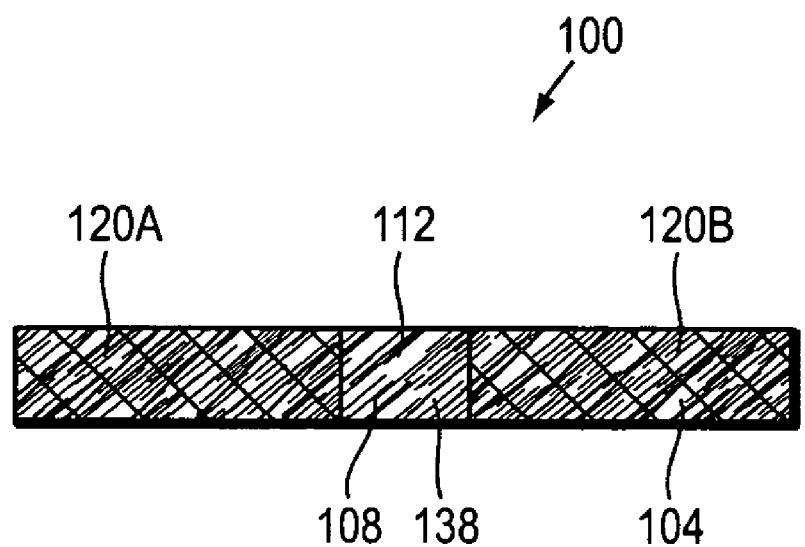
FIG. 3 depicts a top view of a sling assembly according to another illustrative embodiment of the invention.

FIG. 3 depicts a surgical sling assembly 100 according to another embodiment of the invention. As shown, the casing 108 is, in this alternative embodiment, a coating 138. In one embodiment, the coating 138 is applied to the sling 104 by, for example, dipping the sling 104 in, or spraying the sling 104 with, a solution of a bioabsorbable material that later assumes the characteristics of a gel or solidifies. In another embodiment, the coating 138 is a polymer (e.g., a thermoplastic) that is melted, freeze dried, or vacuum dried on to the sling 104. Alternatively, the coating 138 may be applied in a variety of other manners. Moreover, more than one coating 138, of the same or different materials, may be applied, in the same or different manners, to the sling 104. The coating 138 is of sufficient rigidity to prevent the tanged end-length portions 120A, 120B of the sling 104 from catching on the patient's tissues during the delivery procedure.

In one embodiment, the casing 108 (e.g., the sleeve 128 or the coating 138) is made of a biocompatible material. As used herein, the term "biocompatible" means a material that is non-toxic and that does not induce inflammation or any other adverse reaction in the patient's body that would have a significantly adverse effect on the patient's health.

Moreover, in one embodiment, the casing 108 is made of a bioabsorbable material. Accordingly, as explained below, the casing 108 is absorbed by the patient's tissues after the surgical sling assembly 100 is positioned within the patient's periurethral tissues. Advantageously, an operator (e.g., a physician) need not, therefore, remove the casing 108 from about the sling 104 after the sling 104 is implanted in the patient's tissues. Exemplary bioabsorbable materials from which the casing 108 may be made include, but are not limited to, alginates, sugar based formulations, starches, gelatins, cellulose, polyvinyl alcohol, polyglycolic acid (PGA), polylactic acid (PLA), polydioxinone (PDO), and other synthetic and natural polymers including combinations thereof. In another embodiment, the bioabsorbable material is a lubricious material that, during the delivery procedure, reduces the friction between the sling assembly 100 and the patient's periurethral tissues and thereby facilitates placement of the sling assembly 100.

Figure 4:
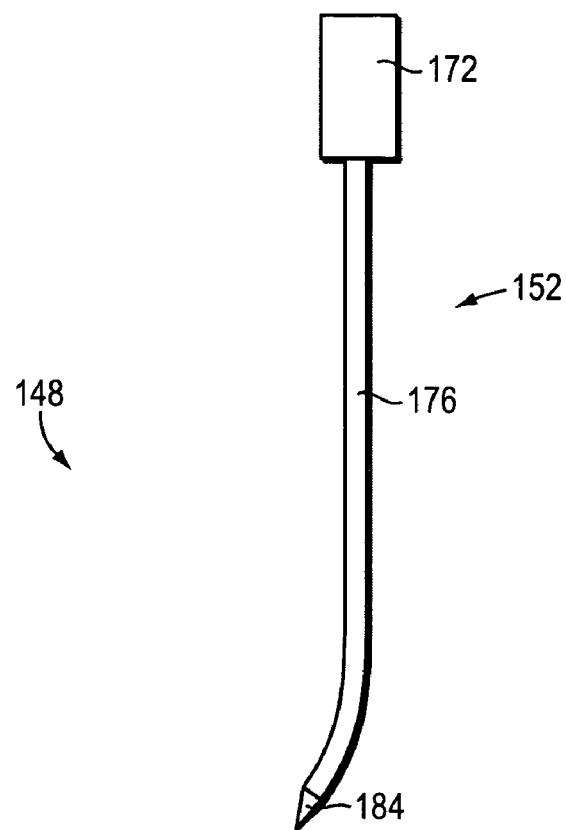
FIG. 4 depicts a perspective view of a delivery system used to deliver a sling assembly to the patient's periurethral tissues in accordance with an illustrative embodiment of the invention.
Figure 4:
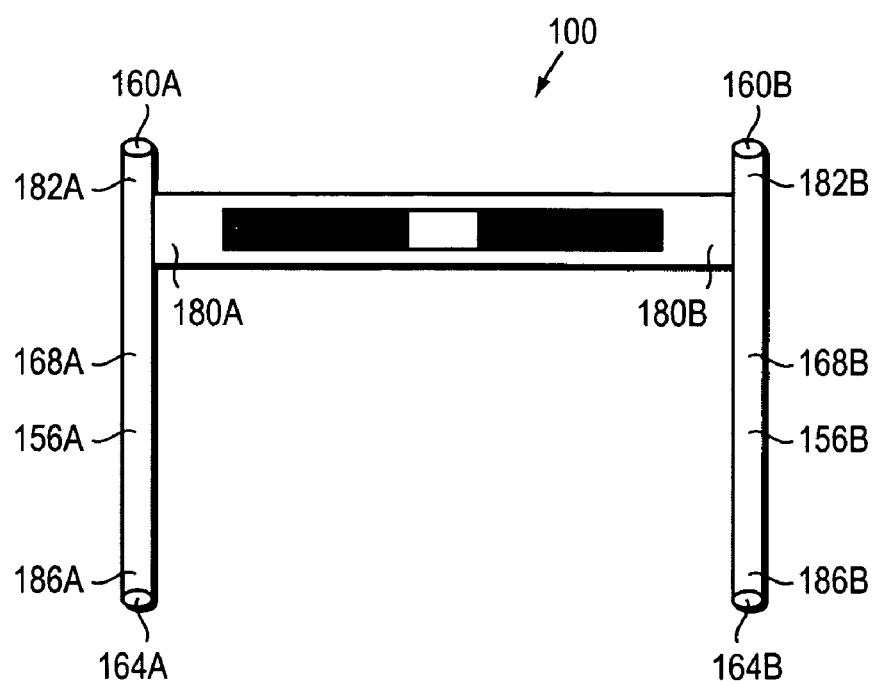

In another aspect, the invention provides a method for treating urinary incontinence. FIG. 4 depicts an exemplary delivery system 148 that is used to deliver the sling assembly 100 to the patient's periurethral tissues in accordance with an illustrative embodiment of the invention. As shown, the delivery system 148 includes a delivery apparatus 152, connectors such as guide tubes 156A, 156B, and the sling assembly 100. In other embodiments, the guide tubes 156A, 156B may be replaced by other types of connectors (not shown). In one embodiment, each of the guide tubes 156A, 156B includes a proximal opening 160, a distal opening 164, and a lumen 168 extending from the proximal opening 160 to the distal opening 164. The exemplary delivery apparatus 152 includes a handle 172 and a cannula 176. In one embodiment, a first end 180A of the sling assembly 100 is coupled to a proximal portion 182A of the first guide tube 156A, and a second end 180B of the sling assembly 100 is coupled to a proximal portion 182B of the second guide tube 156B.

In an exemplary method of treating urinary incontinence, the operator loads the first guide tube 156A onto the cannula 176 illustrated in FIG. 4. Specifically, with continued reference to FIG. 4, a distal end 184 of the cannula 176 is inserted through the proximal opening 160A of the first guide tube 156A. The distal end 184 of the cannula 176 is advanced through the lumen 168A of the first guide tube 156A until it exits from the distal opening 164A of the first guide tube 156A. Illustratively, the operator then introduces the distal end 184 of the cannula 176 into the patient's tissues transvaginally at a first site until the distal end 184 of the cannula 176 emerges once again from the patient's tissues at a second site, such as at the abdominal wall. The operator grasps and stabilizes a distal portion 186A of the first guide tube 156A that emerges from the patient's tissues at the second site. While the operator stabilizes the grasped portion of the first guide tube 156A, the cannula 176 is backed out of the patient's tissues, leaving behind the first guide tube 156A in the patient's tissues. The operator then loads a second guide tube 156B onto the cannula 176 of the delivery apparatus 152 and repeats the above-described procedure on the opposite side of the patient's periurethral tissue.

With both guide tubes 156A, 156B in place in the patient's tissues, the operator performs a cystoscopy to confirm that the guide tubes 156A, 156B have not penetrated the urinary bladder. Once so confirmed, the operator grasps the distal portions 186A, 186B of the guide tubes 156A, 156B, respectively, where they emerge from the patient's tissues at the abdominal wall and withdraws the guide tubes 156A, 156B. The operator then adjusts the position of the sling assembly 100 in the patient's periurethral tissue.

Figure 5:
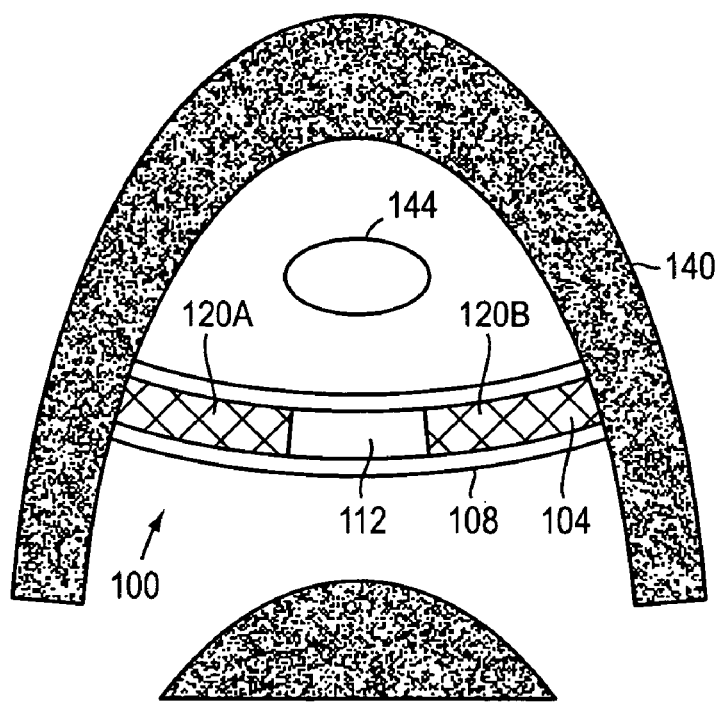
FIG. 5 depicts the placement of a sling assembly, including a bioabsorbable casing, in a patient's periurethral tissues, according to an illustrative embodiment of the invention.

Referring now to FIG. 5, an exemplary method of treating urinary incontinence includes implanting the sling assembly 100, including the sling 104 and the casing 108, in a patient's periurethral tissues 140 and positioning the sling assembly 100 adjacent the patient's urethra 144. In one particular embodiment, an operator places the de-tangled mid-length portion 112 of the sling 104 adjacent the urethra 144. Referring again to FIG. 4, once the sling assembly 100 is correctly positioned, the operator uncouples the ends 180A, 180B of the sling assembly 100 from the guide tubes 156A, 156B. The sling assembly 100, including the sling 104 and the casing 108, is left behind in the patient's periurethral tissues 140, as illustrated in FIG. 5.

In alternative embodiments, rather than using a transvaginal approach as described above, the operator approaches the patient's periurethral tissues 140 using a supra-pubic approach (i.e., percutaneously through the abdominal wall, abdominal fascia, and rectus fascia), a transobturator approach (i.e., around the ischiopubic ramus percutaneously through the obturator membrane and periurethral endopelvic fascia to a vaginal incision), or a pre-pubic approach (i.e., from the abdominal wall along the anterior surface of the pubic bone). Other alternative operable methodologies for placing a sling 104 with a casing 108 according to the invention in a patient's body, to provide anatomical support, are also contemplated within the scope of the invention.

Figure 6:
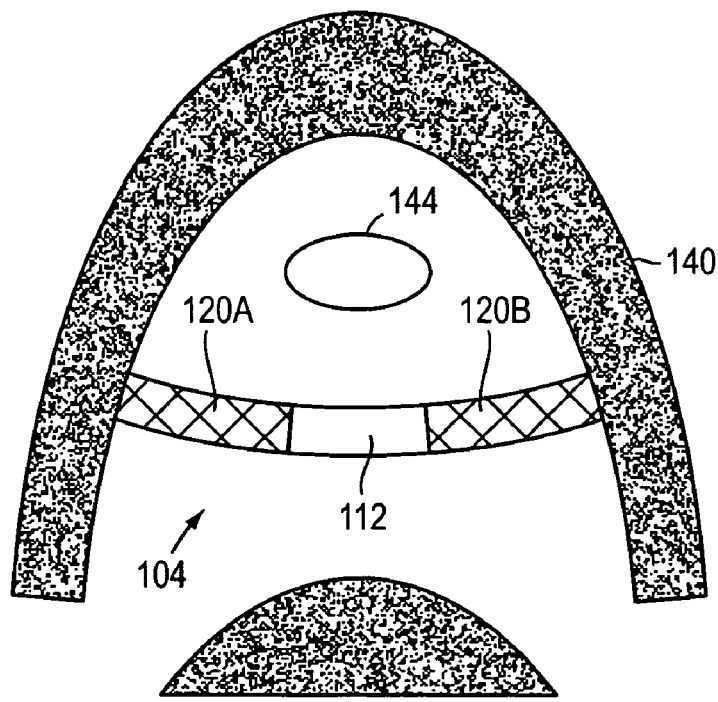
FIG. 6 depicts the placement of a sling in a patient's periurethral tissues, after the casing of FIG. 5 has been absorbed by the patient's tissues, according to an illustrative embodiment the invention.

Referring now to FIG. 6, after a pre-determined period of time, such as, for example, less than ten minutes after placement of the surgical sling assembly 100 in the patient's periurethral tissues 140, the casing 108 is absorbed by the patient's tissues. Preferably, the casing 108 is absorbed by the patient's tissues between eight to ten minutes after placement of the surgical sling assembly 100 in the patient's periurethral tissues 140. However, in alternate embodiments, the casing 108 is absorbed by the patient's tissues after any period of time following placement of the surgical sling assembly 100 in the patient's periurethral tissues 140. Only the sling 104 is left behind in the patient's periurethral tissues 140. Because the operator need not physically remove the casing 108 from about the sling 104 in order to implant the sling 104, the sling 104 is not at risk of shifting, twisting, or of otherwise being misplaced, as would be the case if the casing 108 was physically removed. Advantageously, the de-tangled mid-length portion 112 of the sling 104 remains adjacent the urethra 144. Tissue compression and eventual tissue in-growth at the tangled end-length portions 120A, 120B permanently secure the sling 104 in position. The sling 104 provides the requisite support to assist in maintaining continence.

The sling assembly 100 described above may terminate in any suitable configuration or structure such as loops, apertures, male and female connectors, guide tubes, and the like. Exemplary configurations and structures are disclosed in U.S. patent application Ser. Nos. 10/093,371, 10/093,398, 10/093,424, 10/093,450, 10/093,498, and 10/094,352 filed in the United States Patent Office on Mar. 7, 2002, which are based on and claim priority to provisional patent application Ser. No. 60/274,843 filed in the United States Patent Office on Mar. 9, 2001 and provisional patent application Ser. No. 60/286,863 filed in the United States Patent Office on Apr. 26, 2001, provisional patent application Ser. No. 60/403,555 filed in the United States Patent Office on Aug. 14, 2002, provisional patent application Ser. No. 60/418,827 filed in the United States Patent Office on Oct. 15, 2002, provisional patent application Ser. No. 60/418,642 filed in the United States Patent Office on Oct. 15, 2002, provisional patent application Ser. No. 60/434,167 filed in the United States Patent Office on Dec. 17, 2002, U.S. patent application Ser. No. 10/325,125 filed in the United States Patent Office on Dec. 19, 2002, provisional patent application Ser. No. 60/449,465 filed in the United States Patent Office on Feb. 24, 2003, and provisional patent application Ser. No. 60/465,722 filed in the United States Patent Office on Apr. 25, 2003, all the disclosures of which are hereby incorporated herein by reference in their entirety.

Moreover, the sling assembly 100 of the invention may be employed with any suitable delivery system. Such delivery systems include, for example, those delivery systems configured for supra-pubic, pre-pubic, transvaginal, or transobturator approaches. Without limitation, delivery systems and methodologies that may be employed in combination with the sling assembly 100 of the invention can be found, for example, in U.S. patent application Ser. Nos. 10/093,371, 10/093,398, 10/093,424, 10/093,450, 10/093,498, and 10/094,352 filed in the United States Patent Office on Mar. 7, 2002, which are based on and claim priority to provisional patent application Ser. No. 60/274,843 filed in the United States Patent Office on Mar. 9, 2001 and provisional patent application Ser. No. 60/286,863 filed in the United States Patent Office on Apr. 26, 2001, provisional patent application Ser. No. 60/403,555 filed in the United States Patent Office on Aug. 14, 2002, provisional patent application Ser. No. 60/418,827 filed in the United States Patent Office on Oct. 15, 2002, provisional patent application Ser. No. 60/418,642 filed in the United States Patent Office on Oct. 15, 2002, and provisional patent application Ser. No. 60/434, 167 filed in the United States Patent Office on Dec. 17, 2002, all the disclosures of which are hereby incorporated herein by reference in their entirety.

Additionally, the sling 104 of the invention may have any suitable size or shape configuration and may include any complimentary features. Without limitation, various applicable sling configurations are disclosed in U.S. patent application Ser. No. 09/916,983 filed in the United States Patent Office on Jul. 27, 2001, U.S. patent application Ser. No. 10/092,872 filed in the United States Patent Office on Mar. 7, 2002, provisional patent application Ser. No. 60/388,109 filed in the United States Patent Office on Jun. 12, 2002, provisional patent application Ser. No. 60/403,555 filed in the United States Patent Office on Aug. 14, 2002, provisional patent application Ser. No. 60/449,465 filed in the United States Patent Office on Feb. 24, 2003, provisional patent application Ser. No. 60/465,722 filed in the United States Patent Office on Apr. 25, 2003, and U.S. patent application Ser. No. 10/460,112 filed in the United States Patent Office on Jun. 12, 2003, all the disclosures of which are hereby incorporated herein by reference in their entirety.

Variations, modifications, and other implementations of what is described herein will occur to those of ordinary skill in the art without departing from the spirit and the scope of the invention. The invention is not to be defined only by the preceding illustrative description.

What is claimed is:

1. A surgical sling assembly for implanting in tissue to provide anatomical support in a patient, comprising:
   a sling; and
   a biocompatible casing enclosing at least a portion of the sling, the biocompatible casing comprising a bioabsorbable material,
   wherein the biocompatible casing is not a coating, and
   wherein the biocompatible casing is absorbed by the patient's tissues after the surgical sling assembly is positioned within the patient's tissue to provide anatomical support.

2. The sling assembly of claim 1, wherein the bioabsorbable material comprises an alginate.

3. The sling assembly of claim 1, wherein the bioabsorbable material comprises a sugar based formulation.

4. The sling assembly of claim 1, wherein the bioabsorbable material comprises a starch.

5. The sling assembly of claim 1, wherein the bioabsorbable material comprises a gelatin.

6. The sling assembly of claim 1, wherein the bioabsorbable material comprises cellulose.

7. The sling assembly of claim 1, wherein the bioabsorbable material comprises polyvinyl alcohol.

8. The sling assembly of claim 1, wherein the bioabsorbable material comprises polyglycolic acid.

9. The sling assembly of claim 1, wherein the bioabsorbable material comprises polylactic acid.

10. The sling assembly of claim 1, wherein the bioabsorbable material comprises polydioxinone.

11. The sling assembly of claim 1, wherein the bioabsorbable material comprises a lubricious material.

12. The sling assembly of claim 1, wherein the surgical sling assembly is adapted for positioning within a patient's periurethral tissues to treat urinary incontinence.

13. The sling assembly of claim 12, wherein the biocompatible casing is absorbed by the patient's tissues in less than ten minutes after the surgical sling assembly is positioned within the patient's periurethral tissues.

14. The sling assembly of claim 13, wherein the biocompatible casing is absorbed by the patient's tissues in eight to ten minutes after the surgical sling assembly is positioned within the patient's periurethral tissues.

15. The sling assembly of claim 1, wherein the biocompatible casing comprises a sleeve.

16. The sling assembly of claim 15, wherein the sleeve is a flattened tube.

17. The sling assembly of claim 1, wherein the sling comprises one or more tanged portions.

18. The sling assembly of claim 17, wherein the sling comprises two tanged end portions.

19. The sling assembly of claim 1, wherein the sling comprises a de-tanged portion.

20. The sling assembly of claim 1, wherein the sling comprises a de-tanged mid-length portion.

21. The sling assembly of claim 1, further comprising one or more guide tubes located at one or more ends of the sling assembly.

22. The sling assembly of claim 1, further comprising a delivery apparatus comprising:
   a handle, and
   a cannula.

23. A method for providing anatomical support in a patient, comprising: providing a surgical sling assembly, comprising:
   a sling; and
   a biocompatible casing enclosing at least a portion of the sling, the biocompatible casing comprising a bioabsorbable material,
   wherein the biocompatible casing is not a coating, and
   wherein the biocompatible casing is absorbed by the patient's tissues after the surgical sling assembly is positioned within the patient's tissue to provide anatomical support; and
   positioning the sling within the patient's tissue to provide anatomical support in the patient.

24. The method of claim 23, wherein positioning the sling comprises positioning the sling within a patient's periurethral tissues to treat urinary incontinence.

25. A surgical sling assembly for implanting in tissue to provide anatomical support in a patient, comprising:
   a sling; and
   a biocompatible sleeve comprising a bioabsorbable material,
   wherein the sling is at least partially movable with respect to the sleeve, and
   wherein the biocompatible sleeve is absorbed by the patient's tissues after the surgical sling assembly is positioned within the patient's tissue to provide anatomical support.

* * * * *